United States Patent [19]

Annis et al.

[11] Patent Number: 5,253,283
[45] Date of Patent: Oct. 12, 1993

[54] INSEPCTION METHOD AND APPARATUS WITH SINGLE COLOR PIXEL IMAGING

[75] Inventors: Martin Annis, Cambridge, Mass.; Gerard P. Riley, Chester, N.H.

[73] Assignee: American Science and Engineering, Inc., Cambridge, Mass.

[21] Appl. No.: 811,685

[22] Filed: Dec. 23, 1991

[51] Int. Cl.$^5$ ............................................. H05G 1/64
[52] U.S. Cl. .................................. 378/100; 378/46; 378/62; 378/90
[58] Field of Search ............... 378/44, 46, 51, 62, 378/86, 87, 90, 99, 100; 358/111

[56] References Cited

U.S. PATENT DOCUMENTS

| | | |
|---|---|---|
| 3,673,317 | 6/1972 | Newell et al. ............... 378/100 |
| 3,848,130 | 11/1974 | Macovski ....................... 378/100 |
| 3,927,318 | 12/1975 | Macovski ....................... 378/100 |
| 4,799,247 | 1/1989 | Annis . |
| 4,987,584 | 1/1991 | Doenges . |

FOREIGN PATENT DOCUMENTS 0143751 7/1985 Japan ........................... 378/100

Primary Examiner—David P. Porta
Attorney, Agent, or Firm—Pollock, Vande Sande & Priddy

[57] ABSTRACT

An inspection system using penetrating radiation wherein pixels corresponding to transmitted radiation which has been attenuated to at least a predetermined level are displayed in a first color. Pixels which correspond to radiation which has been backscattered to a least predetermined level are displayed in a second color, and pixels which correspond to the remainder of the transmitted radiation are displayed in a third color. Additionally, the brightness of the color of each pixel is controlled in dependence on how far above or below the predetermined level the detected transmitted or scattered signal is.

12 Claims, 1 Drawing Sheet

INSEPCTION METHOD AND APPARATUS WITH SINGLE COLOR PIXEL IMAGING

The present invention is directed to an inspection system having a color display.

In recent years, inspection systems which use penetrating radiation have been widely used. For example, such systems are commonly used to inspect containers such as parcels or baggage for contraband.

It is important that the information which is detected by such systems be conveyed to an operator in a form which allows quick and accurate identification of contraband. Thus, operators of such equipment, who may be required to continuously review images of objects which are being rapidly processed over long periods of time, cannot afford to make a mistake. Since operator fatigue may become a factor, it is desirable for the images which are displayed to be in a vivid, attention maintaining format. And, since operators may sometimes need to be trained quickly, it is desirable for the visual format which is used to be easily learned and employed.

Inspection systems may use both radiation which is transmitted through objects which are inspected, and radiation which is scattered from such objects. Thus, over certain thicknesses, objects which have a high atomic number or Z, such as metals tend to attenuate more radiation than they scatter, while objects which have a low Z such as plastics, again over a reasonable range of thicknesses, tend to scatter more radiation than they attenuate. Since contraband may be comprised of both high Z objects, e.g., metal guns, and low Z objects, e.g., plastic explosives or narcotics, it is desirable to be presented with an image having information which corresponds to both transmitted and scattered radiation.

In the equipment of the prior art, images are typically presented in a scale of gray tones wherein black may represent highly attenuated transmitted energy and white may represent highly scattered energy, and the transmitted and scattered energy may be presented on separate displays. Such images of gray tones may be difficult for an operator to quickly or accurately interpret. Additionally, a large number of rapidly passing gray tone images may become monotonous to watch.

To obviate this problem, it has heretofore been proposed to use color images. Thus, a system has been suggested wherein transmitted energy would correspond to two colors and scattered energy would correspond to another color, and the images would be superimposed. Since many areas of the image will correspond to both transmitted and scattered energy, the superposition of such color images may lead to a composite which is difficult to interpret.

In a prior art system used for medical imaging which utilizes only transmitted radiation, the range of gray tones which is usually displayed is replaced with a range of different colors. Since a continuum of all colors is used, such a display may also not be easy to interpret quickly.

U.S. Pat. No. 4,987,584 discloses an inspection system which uses transmitted energy in multiple energy bands. By mathematically processing the attenuation in the respective energy bands, information about the material makeup of the illuminated object may be obtained. Such multiple energy band inspection systems are generally more complex than systems which operate within a single energy band. In the system of the above-mentioned patent, each pixel is displayed in one of three colors in accordance with a first function of the transmitted energy in the different energy bands, while the shade of the color of each pixel is controlled in accordance with a second function of the transmitted energy in the different energy bands.

It is thus the object of the present invention to provide an inspection method and apparatus which displays information in a manner which facilitates rapid and accurate identification of contraband.

This object is accomplished by illuminating an object to be inspected with penetrating radiation, receiving radiation which is transmitted through the object and radiation which is scattered by the object, displaying pixels which correspond to attenuated radiation of at least a certain level in a first predetermined, single color, and displaying pixels which correspond to scattered radiation of at least a certain level in a second, predetermined single color.

In the preferred embodiment of the invention, three colors are used to display the three types of materials which are of the most importance, as follows:

a) pixels which represent more than a predetermined level of attenuation.

b) pixels which represent more than a predetermined level of backscatter, and c) the remainder of the energy which is transmitted through the object.

Additionally, the brightness of the color is controlled in accordance with the magnitude of the signal. Thus, pixels which fall within the first category are displayed in a first color, e.g., blue, with pixels close to a first predetermined level of attenuation being displayed in a medium blue, with the shade of the color becoming brighter as the magnitude of the attenuation increases.

Pixels corresponding to the second category are displayed in a second color, e.g, red, with the brightness of the color increasing from medium red to bright red as the level of backscatter increases above a second predetermined level.

Finally, pixels corresponding to the third category are displayed in a third color, for example, green, with the brightness of the color increasing as the level of attenuation decreases below the first predetermined level. Additionally, there is a priority involved in display of the colors. For example, if a pixel meets both criteria a) and b) above, it is displayed in the color allocated to criterion b), e.g., red. Additionally, pixels are displayed in the color allocated to criterion c), e.g., green, only when neither criterion a) or b) is met.

In accordance with an aspect of the invention, all transmitted energy signals may be displayed in pixels of one color, while all backscattered energy signals may be displayed in pixels of another color. Additionally, the brightness of the colors may be controlled in accordance with the magnitude of the transmitted or backscattered energy signal.

The invention will be better appreciated by referring to the accompanying drawings, wherein.

Figure 1:
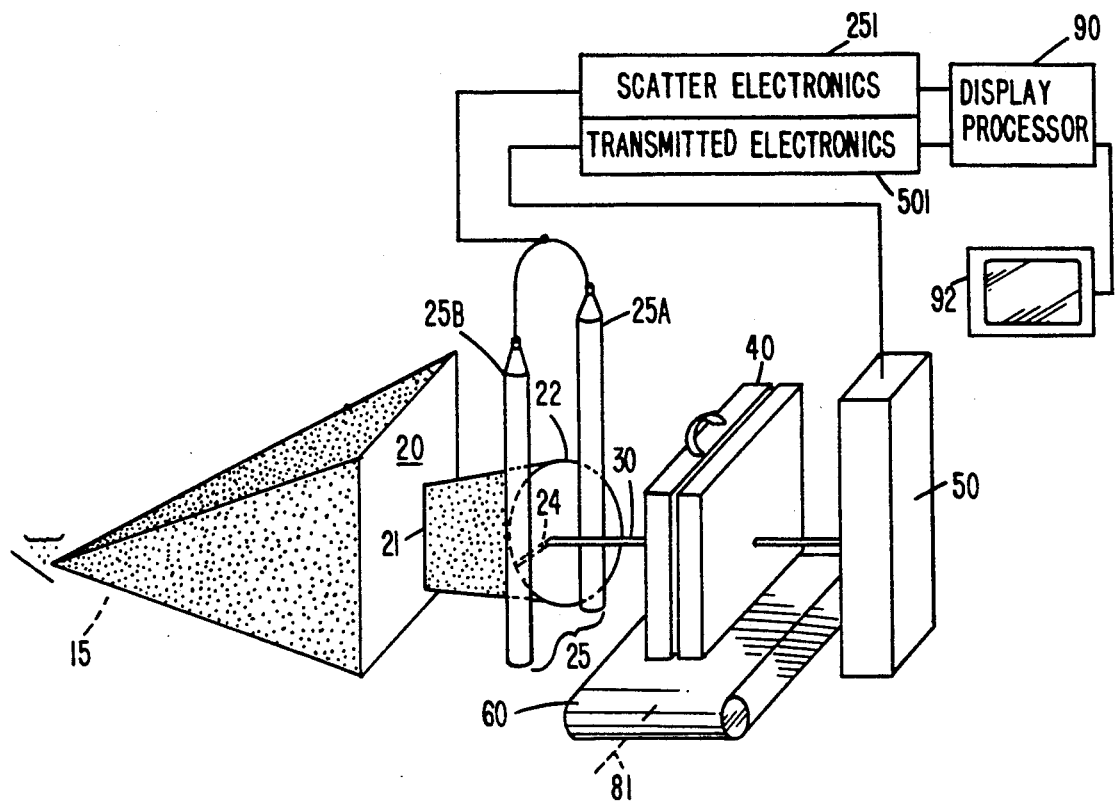
FIG. 1 is a pictorial illustration of apparatus which utilizes the invention.

Referring to FIG. 1, a system for inspecting object 40, which is moving on conveyor 80, past transmission detector 50 and backscatter detectors 25A and 25B, is depicted. Part of this system is described in detail in U.S. Pat. No. 4,799,247, which is incorporated herein by reference.

Referring to the figure, a flying spot scanner, which is comprised of slitted plate 20 and slitted chopper wheel 22 produces a flying spot pencil x-ray beam 30 which repeatedly sweeps up along the transmit detector 50 after passing through object 40. The detector 50 converts the beam which has been attenuated by object 40 into an electrical signal which is fed to the transmitted electronics 501. At the same time, the object 40, or more particularly the components which are contained within object 40, scatter x-radiation. Some of the scattered radiation which is scattered back in the direction of the source impinges on the backscatter detector 25, and is converted into an electrical signal which is fed to the scatter electronics 251.

The source/detector arrangement which is described in FIG. 1 has the characteristic that the signals in any instant in time produced by either the detector 50 or the backscatter detector 25 can be mapped to a particular region of the object 40 whose illumination produced the resulting signal. Accordingly, as those skilled in the art are aware, a signal, or a group of signals (suitably averaged or combined) can be used to represent a pixel, an elementary portion of an image that will be formed and displayed. The pixel, or the signal which is generated to produce the pixel, has an amplitude or intensity. In the case of the transmitted beam detected by the transmission detector 50, the intensity of the pixel can be used to represent the attenuation presented to the illumination beam by the portion of the object 40 which was illuminated when the pixel was generated. By like token, the intensity of the pixel generated by the backscatter detector can be mapped to that region of the object 40 whose illumination by the penetrating pencil beam 30 produced the backscattered x-rays which generated the pixel.

The backscatter signal is dependent on the density along one line of sight of the pencil beam 30, the distribution of the density along that line of sight, and the distance between each elemental mass and the backscatter detector 25. More particularly, both high Z and low Z components of the object 40 produce both attenuation and scatter. However for certain object thicknesses, for high Z objects, the x-ray absorption is more pronounced than scatter whereas, again for a reasonable range of thicknesses, for low Z objects, scatter predominates over absorption. Furthermore, the intensity of the backscatter signal for a given low Z object also varies (non-linearly) with thickness. In other words, as the thickness increases, the backscatter signal will also increase. As those skilled in the art are aware, the backscatter intensity is also dependent on density. As a result, variations in density in the line of sight of the pencil beam 30 produce variations in the backscatter intensity. To the extent that the mass within the line of sight has a both constant thickness and density, the backscatter signal intensity will also remain relatively constant, whereas if the line of sight density and thickness varies, the backscatter signal intensity would also vary.

After the detected transmission and scatter signals are processed in transmitted electronics 501 and scatter electronics 251, which as known to those skilled in the art, include suitable amplifiers, A/D converters, and timing circuitry, they are fed to color display processor 90, which forms the correct color output signals for driving color monitor 92.

Figure 2:
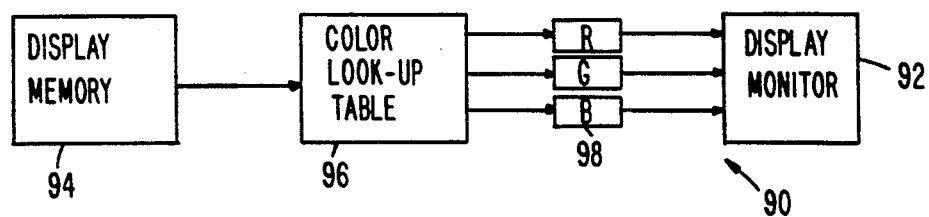
FIG. 2 is a block diagram of an embodiment of the processing which is accomplished by the invention.

FIG. 2 is a block diagram of the color display processor 90, which is seen to include display memory 94, color look-up table 96, and D/A converters 98. In the operation of the system, transmitted electronics 501 and scatter electronics 251 output coded statuses to display memory 94 which are indicative of the intensity of the transmitted and scattered signal for each pixel. Thus, each storage location of display memory 94 has stored therein such coded statuses.

The coded statuses representative of the intensity of the transmitted and scattered signal for each pixel are fed to color look-up table 96, which allocates one of three colors as well as a shade of the particular color to the respective coded statuses for each pixel. The signals corresponding to each of the three colors are fed to separate D/A converters 98 for providing suitable signals for driving color cathode ray tube monitor 92.

In accordance with an aspect of the invention, the programming of color look-up table 96 is arranged so that only the three types of materials in the object being inspected which are of the most interest are depicted in three unique colors.

The three most important types of materials are:

(a) those which attenuate more than a first predetermined level of radiation. For example, in the preferred embodiment this is a relatively high level (e.g. 90%), but the level may be changed in dependence on the particular application;

(b) those which backscatter more than a predetermined percentage of some maximum reference backscatter level (e.g. 45%); and (c) those which transmit the remainder of the transmitted radiation.

Additionally, the color look-up table allocates a shade of the particular color, again depending on the intensity of the signals which correspond to the transmitted and scattered radiation. In the preferred embodiment of the invention, the shade of the color of the pixels corresponding to the materials described in categories (a) and (b) above is made brighter as the intensity of the signal increases above the predetermined level, while the color corresponding to the material described in category (c) is made brighter as the intensity of the signal decreases below the predetermined level.

As an example of a color scheme which may be advantageously employed with the invention, pixels corresponding to category (b) above may be displayed in the color red, with pixels corresponding to signals which are just above the predetermined level being displayed in light red, with the brightness increasing as the signal increases above the predetermined level. Pixels which correspond to category (a) above may be displayed in blue with pixels corresponding to signals which are just above the predetermined level being displayed in medium blue, with the color becoming brighter as the attenuation of the signal increases. Finally, pixels which correspond to category (c) above may be displayed in green, from light green for pixels which are just below the first, predetermined level of attenuation to bright green for pixels which correspond to very little attenuation. A zero attenuated signal is displayed in black to remove the background from the inspected item to further highlight the item being inspected.

Furthermore, there is a priority allocated to the display of the colors, which is included in the color look up table. That is, if a pixel falls into both categories a) and b), category b) dominates, and the pixel is displayed in the color allocated to represent a high degree of scattered radiation, e.g., red. Additionally, a pixel is displayed in the color allocated to category c), e.g., green, only when the pixel does not fall into category a) or b).

There thus is provided a display wherein each pixel has a unique recognizable color to provide quick and accurate identification of materials and objects, and wherein there is no mixing of colors. By displaying only the three most important types of materials in the object being inspected in three discrete colors, ambiguities are minimized or eliminated, and the operator is presented with a display which can be rapidly evaluated.

While the preferred embodiment of the invention has been described in connection with a display of three colors corresponding to the types of materials in categories (a), (b) and (c) above, it should be appreciated that the invention might also be advantageously employed to provide images which display only two of the three categories.

In accordance with a further aspect of the invention, an option is provided wherein pixels corresponding to all of the transmitted radiation can be displayed in a single color, e.g. blue or green, and pixels corresponding to all of the scattered energy can be displayed in a single color, e.g. red. To achieve this option, the look-up table 96 would be programmed to allocate the respective color to coded statuses for each pixel fed out of display memory 94 which corresponded to transmitted and scattered energy respectively.

Furthermore, the look-up table may be programmed so as to allocate a brightness value to the particular color for each pixel which is dependent on the intensity of the transmitted or scattered radiation. Hence, the transmission and scatter images which are displayed on color monitor 92 would depict the spatial variations in transmitted and scattered radiation.

The option described above may be useful in the case where the operator after having observed the image in three colors, desires to have a closer look at separate images of transmitted and scattered energy.

There thus has been described an inspection system having many advantages. While the invention has been described in connection with preferred and illustrative embodiments, it should be understood that variations will occur to those skilled in the art, and the invention is to be limited only by the claims appended hereto and equivalents.

We claim:

1. A method of displaying information resulting from the inspection of an object with penetrating radiation, comprising the steps of,
    after an object has been illuminated with penetrating radiation, receiving radiation which corresponds to a first type of interaction with said object and radiation which corresponds to a second type of interaction with said object,
    displaying pixels which correspond to at least a first presettable level of said first type of interaction in a first predetermined single color, and
    displaying pixels which correspond to at least a second presettable level of said second type of interaction in a second, predetermined single color.

2. The method of claim 1 wherein pixels which correspond to both at least said firs presettable level of said first type of interaction and at least said second presettable level of said second type of interaction as displayed in said second, predetermined single color.

3. The method of claim 1 wherein said first type of interaction is the attenuation of radiation by said object and said second type of interaction is the backscattering of radiation by said object.

4. The method of claim 3 further including the step of controlling the brightness of said first and second colors depending on the magnitude of the received radiation corresponding to said first and second types of interaction.

5. An apparatus for displaying information resulting from the inspection of an object with penetrating radiation, comprising:
    means for illuminating an object with penetrating radiation,
    means for receiving radiation which is transmitted through said object,
    means for receiving radiation which is backscattered from said object,
    means for displaying pixels which correspond to at least a first presettable level of attenuation of the transmitted radiation in a first predetermined single color, and
    means for displaying pixels which correspond to at least a second presettable level of backscattered radiation in a second predetermined single color.

6. The apparatus of claim 5, further including:
    means for displaying pixels which correspond to transmitted radiation which is attenuated less than said first presettable level of attenuation in a third predetermined single color.

7. A method of displaying information resulting from the inspection of an object with penetrating radiation, comprising the steps of,
    after an object has been illuminated with penetrating radiation, receiving radiation which corresponds to a first type of interaction with said object and radiation which corresponds to a second type of interaction with said object,
    displaying pixels which correspond to at least a first presettable level of said first type of interaction in a first predetermined single color, and
    displaying pixels which correspond to at least a second presettable level of said second type of interaction in a second, predetermined single color, and
    displaying pixels which correspond to less than one of said first and second levels in a third predetermined single color.

8. A method of displaying information resulting from the inspection of an object with penetrating radiation, comprising the steps of,
    illuminating an object with penetrating radiation,
    after said radiation interacts with said object, receiving radiation which is transmitted through said object and radiation which is backscattered from said object,
    displaying pixels which correspond to at least a first presettable level of attenuation of the transmitted radiation in a first predetermined single color, and
    displaying pixels which correspond to at least a second presettable level of backscattered radiation in a second predetermined single color.

9. The method of claim 8 comprising the step of,
    displaying pixels which correspond to transmitted radiation which is attenuated less than said first presettable level of attenuation in a third predetermined single color.

10. The method of claim 8 wherein the brightness of said first color is controlled in dependence on how far above said first presettable level of attenuation, the attenuation of said transmitted radiation which is received is, and wherein the brightness of said second color is controlled in dependence on how far above said second presettable level of backscattered radiation, the received backscattered radiation is.

11. The method of claim 9 wherein the brightness of said first color is controlled in dependence on how far above said first presettable level of attenuation, the attenuation of said transmitted radiation which is received is, and wherein the brightness of said second color is controlled in dependence on how far above said second presettable level of backscattered radiation, the received backscattered radiation is.

12. The method of claim 11 wherein the brightness of said third color is controlled in dependence on how far beneath said first presettable level of attenuation said transmitted radiation which is received is.

* * * * *